United States Patent
Kamata

(10) Patent No.: US 12,076,195 B2
(45) Date of Patent: Sep. 3, 2024

(54) MEDICAL HOLDING APPARATUS

(71) Applicant: Sony Olympus Medical Solutions Inc., Tokyo (JP)

(72) Inventor: Yoshiyuki Kamata, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 918 days.

(21) Appl. No.: 16/980,848

(22) PCT Filed: Feb. 1, 2019

(86) PCT No.: PCT/JP2019/003748
§ 371 (c)(1),
(2) Date: Sep. 15, 2020

(87) PCT Pub. No.: WO2019/181239
PCT Pub. Date: Sep. 26, 2019

(65) Prior Publication Data
US 2021/0015582 A1    Jan. 21, 2021

(30) Foreign Application Priority Data
Mar. 22, 2018    (JP) .................. 2018-054142

(51) Int. Cl.
*A61B 90/25*    (2016.01)
*A61B 90/00*    (2016.01)
(Continued)

(52) U.S. Cl.
CPC .......... *A61B 90/25* (2016.02); *B25J 13/085* (2013.01); *A61B 2090/067* (2016.02); *G02B 21/0012* (2013.01); *G02B 21/24* (2013.01)

(58) Field of Classification Search
CPC .............. A61B 90/25; A61B 2090/067; A61B 2090/064; A61B 34/30; A61B 90/50; B25J 13/085; G02B 21/0012
See application file for complete search history.

(56) References Cited

U.S. PATENT DOCUMENTS 6,522,952 B1 *  2/2003  Arai .............. B25J 9/1679
                                              700/258
2015/0224643 A1  8/2015  Ernsperger
2019/0059991 A1 *  2/2019  Shelton, IV ......... A61B 34/35

FOREIGN PATENT DOCUMENTS

JP   10-249769 A    9/1998
JP   2004-329762 A  11/2004
(Continued)

OTHER PUBLICATIONS

International Search Report and Written Opinion mailed on Apr. 23, 2019 for PCT/JP2019/003748 filed on Feb. 1, 2019, 9 pages including English Translation of the International Search Report.

*Primary Examiner* — Lynsey C Eiseman
*Assistant Examiner* — Daniel Tehrani
(74) *Attorney, Agent, or Firm* — XSENSUS LLP

(57) ABSTRACT

A medical holding apparatus includes: an arm including a plurality of links mutually coupled through one of joints, the arm having at least six degrees of freedom due to rotational motion about a rotation axis, the arm being configured to function as a balanced arm with a counterweight and support a medical device; and an arm controller configured to control motion of the arm, in which at least three of the joints in the arm each are provided with an angular sensor that detects a rotation angle of the rotation axis and an actuator that gives the joint an assist force of assisting the rotational motion, and the arm controller controls, based on respective detected results of the angular sensors, the respective assist forces of the actuators such that an amount of force in operation necessary when an operator moves the medical device supported by the arm remains in a predetermined range.

17 Claims, 6 Drawing Sheets

(51) Int. Cl.
*B25J 13/08* (2006.01)
*G02B 21/00* (2006.01)
*G02B 21/24* (2006.01)

(56) References Cited

FOREIGN PATENT DOCUMENTS

| | | |
|---|---|---|
| JP | 2017177290 A | 10/2017 |
| WO | WO-2015137040 A1 | 9/2015 |
| WO | 2016/017532 A1 | 2/2016 |
| WO | 2017/169649 A1 | 10/2017 |

* cited by examiner

MEDICAL HOLDING APPARATUS

CROSS-REFERENCE TO RELATED APPLICATIONS

The present application is based on PCT filing PCT/JP2019/003748, filed Feb. 1, 2019, which claims priority to JP 2018-054142, filed Mar. 22, 2018, the entire contents of each are incorporated herein by reference.

TECHNICAL FIELD

The present disclosure relates to a medical holding apparatus.

BACKGROUND ART

In recent years, in medical institutions, for example, for supporting microsurgery, such as neurosurgical operations, or for endoscopic surgery, in some cases, used is a medical observation apparatus enabling magnification and observation of a target to be observed, such as an affected part. Examples of the medical observation apparatus include a medical observation apparatus including an optical microscope and a medical observation apparatus including an imaging device that functions as an electronic-imaging microscope. Hereinafter, the medical observation apparatus including an optical microscope is referred to as an "optical medical observation apparatus". In addition, hereinafter, the medical observation apparatus including an imaging device is referred to as an "electronic-imaging medical observation apparatus". In addition, hereinafter, an imaged image (moving image or still image) including a target to be observed imaged by the imaging device included in the electronic-imaging medical observation apparatus is referred to as a "medical imaged image".

In a medical observation apparatus, such as the optical medical observation apparatus or the electronic-imaging medical observation apparatus, the optical microscope or the imaging device is supported by an arm having a predetermined degree of freedom. Then, an operator who operates the medical observation apparatus, such as a surgical operator or an assistant to the surgical operator, can move the optical microscope or the imaging device freely in the movable range of the arm corresponding to the degree of freedom.

In such a situation, a technology of achieving improvement in operability for an operator who operates a medical observation apparatus has been developed. Regarding a surgical microscope (corresponding to the optical medical observation apparatus), a technology of preventing the arm of the microscope from interfering with an observer to achieve improvement in operability is, for example, the technology in Patent Literature 1 below.

CITATION LIST

Patent Literature

Patent Literature 1: JP 2004-329762 A

DISCLOSURE OF INVENTION

Technical Problem

For example, in a case where the amount of force in operation necessary "when an operator who operates a medical observation apparatus moves the optical microscope or the imaging device supported by the arm" varies significantly depending on the posture of the arm, the operator is likely to fatigue in operation. Here, as a method of reducing the possibility that the operator fatigues in operation, it can be thought that the amount of force in operation is uniformed.

However, existing technology, like the technology in Patent Literature 1, has not taken account of uniforming the amount of force in operation. Thus, even with the existing technology, it is difficult to uniform the amount of force in operation.

In addition, for example, an existing apparatus including an arm supporting a medical device, like an endoscope holder, is incapable of uniforming the amount of force in operation, similarly. Hereinafter, "a medical observation apparatus, such as the optical medical observation apparatus or the electronic-imaging medical observation apparatus," and an apparatus including an arm supporting a medical device, like an endoscope holder, are referred to as a "medical holding apparatus".

That is, because an existing medical holding apparatus is incapable of uniforming the amount of force in operation, an operator who operates the medical holding apparatus (e.g., a medical expert, such as a surgical operator or an assistant to the surgical operator, hereinafter, also simply referred to as an "operator") is likely to feel fatigued due to operation.

An object of the present disclosure is to propose a novel and improved medical holding apparatus enabling achievement of improvement in operability for an operator. Solution to Problem According to the present disclosure, there is provided a medical holding apparatus including: an arm including a plurality of links mutually coupled through one of joints, the arm having at least six degrees of freedom due to rotational motion about a rotation axis, the arm being configured to function as a balanced arm with a counterweight and support a medical device; and an arm controller configured to control motion of the arm, wherein at least three of the joints in the arm each are provided with an angular sensor that detects a rotation angle of the rotation axis and an actuator that gives the joint an assist force of assisting the rotational motion, and the arm controller controls, based on respective detected results of the angular sensors, the respective assist forces of the actuators such that an amount of force in operation necessary when an operator moves the medical device supported by the arm remains in a predetermined range.

Advantageous Effects of Invention

According to the present disclosure, improvement in operability for an operator can be achieved.

Note that the effect is not necessarily limitative and thus, in addition to the effect or instead of the effect, any effect in the present specification or other effects to be grasped from the present specification may be produced.

BEST MODE FOR CARRYING OUT THE INVENTION

A preferred embodiment of the present disclosure will be described in detail below with reference to the accompanying drawings. Note that, in the present specification and the drawings, constituent elements having substantially the same functional configurations are denoted with the same reference signs, and the duplicate descriptions thereof will be omitted.

In addition, the description will be given in the following order.

1. Configuration of Medical Holding Apparatus according to Present Embodiment and Control Method according to Present Embodiment
   [1] Configuration of Medical Holding Apparatus according to Present Embodiment
   [2] Control Method according to Present Embodiment
   [3] Exemplary Effects due to Use of Medical Holding Apparatus according to Present Embodiment
2. Program according to Present Embodiment (Medical Observation System according to Present Embodiment and Control Method according to Present Embodiment)

An exemplary medical holding apparatus according to the present embodiment will be described below, and additionally a control method according to the present embodiment will be described below.

An exemplary case where the medical holding apparatus according to the present embodiment is an electronic-imaging medical observation apparatus, namely, a medical observation apparatus including an arm supporting an imaging device (exemplary medical device), will be given below. Note that the medical holding apparatus according to the present embodiment is not limited to the electronic-imaging medical observation apparatus. For example, the medical holding apparatus according to the present embodiment can be applied to an optical medical observation apparatus or any medical apparatus including an arm supporting a medical device, such as an endoscope holder.

[1] Configuration of Medical Holding Apparatus According to Present Embodiment

Figure 1:
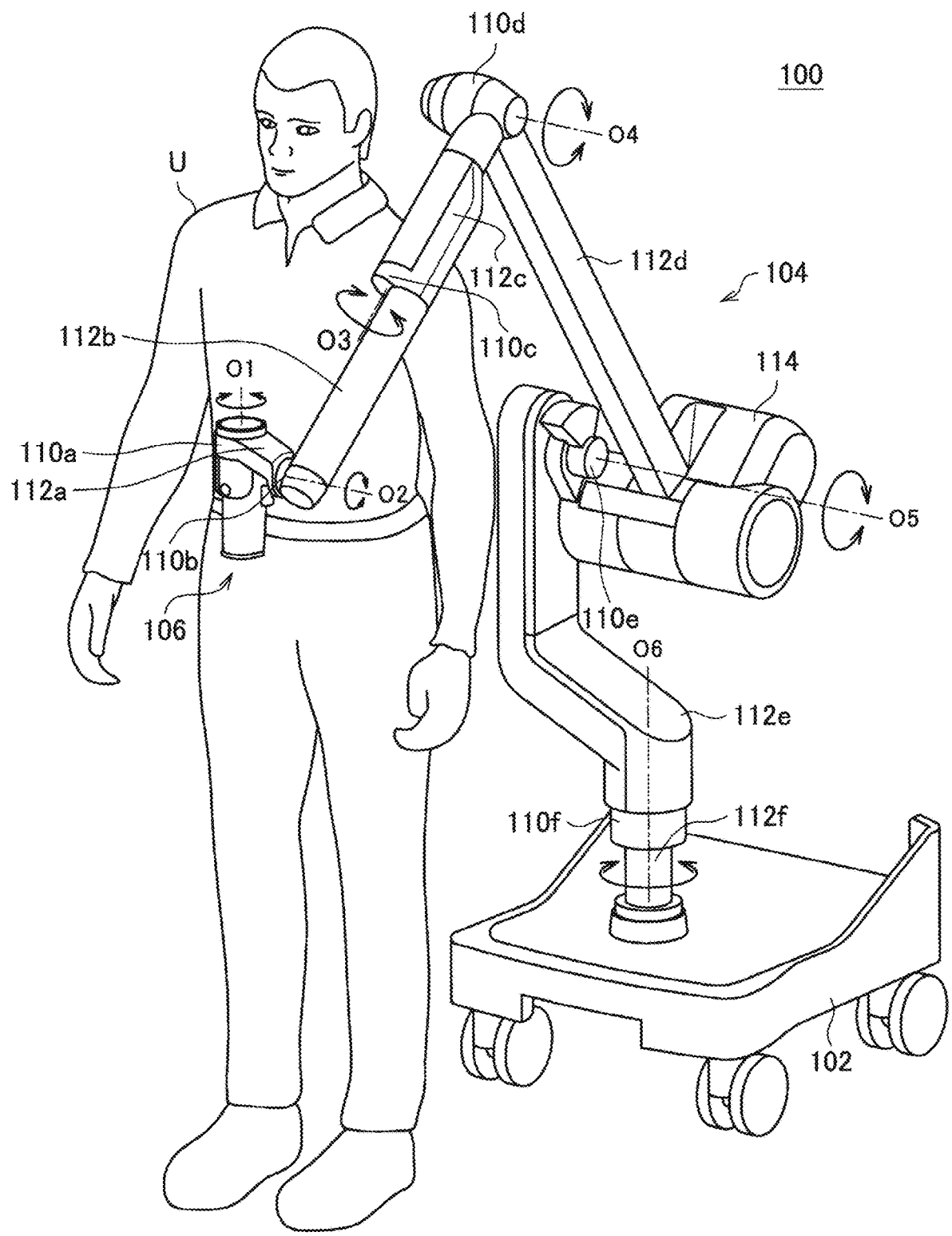
FIG. 1 is an explanatory view illustrating an exemplary configuration of a medical holding apparatus according to the present embodiment.

FIG. 1 is an explanatory view illustrating an exemplary configuration of a medical holding apparatus 100 according to the present embodiment. With the exemplary configuration, the medical holding apparatus 100 functions as an electronic-imaging medical observation apparatus. FIG. 1 illustrates an operator U together with the medical holding apparatus 100.

For example, in a case where the medical holding apparatus 100 is used at the time of surgery, a surgical operator (exemplary operator of the medical holding apparatus 100) observes a surgical site (affected part) with reference to a medical imaged image that is imaged by the medical holding apparatus 100 and is displayed on the display screen of any display device. The surgical operator gives the surgical site various types of treatment, such as a procedure corresponding to a surgical approach.

The medical holding apparatus 100 includes, for example, a base 102, an arm 104, and an imaging device 106.

In addition, although not illustrated in FIG. 1, the medical holding apparatus 100 may include, for example, at least one processor (not illustrated) including an arithmetic circuit, such as a micro processing unit (MPU), a read only memory (ROM, not illustrated), a random access memory (RAM, not illustrated), a recording medium (not illustrated), and a communication device (not illustrated). For example, the medical holding apparatus 100 is driven by power supplied from an internal power source, such as a battery, included in the medical holding apparatus 100 or by power supplied from an external power source in connection with the medical holding apparatus 100.

The at least one processor (not illustrated) functions as a control unit (to be described later) in the medical holding apparatus 100. The ROM (not illustrated) stores a program and control data, such as arithmetic parameters, to be used by the at least one processor. The RAM (not illustrated) temporarily stores, for example, a program to be executed by the at least one processor (not illustrated).

The recording medium (not illustrated) functions as a storage unit (not illustrated) in the medical holding apparatus 100. The recording medium (not illustrated) stores, for example, data according to the control method according to the present embodiment, such as a set value (to be described later), and various types of data, such as various types of applications. Here, examples of the recording medium (not illustrated) include a magnetic recording medium, such as a hard disk, and a nonvolatile memory, such as a flash memory. In addition, the recording medium (not illustrated) may be detachable from the medical holding apparatus 100.

The communication device (not illustrated) that is communication means included in the medical holding apparatus 100, serves to communicate with an external device, such as a display device, by wireless or by wire. Here, examples of the communication device (not illustrated) include an IEEE802.15.1 port and a transmitting and receiving circuit (wireless communication), an IEEE802.11 port and a transmitting and receiving circuit (wireless communication), a communication antenna and a radio frequency (RF) circuit (wireless communication), and a local area network (LAN) terminal and a transmitting and receiving circuit (wired communication).

[1-2-1] Base 102

The base 102 is the foundation of the medical holding apparatus 100. The base 102 in connection with one end of the arm 104 supports the arm 104 and the imaging device 106.

In addition, the base 102 is provided with, for example, casters, so that the medical holding apparatus 100 has contact with a floor through the casters. The provision of the casters enables the medical holding apparatus 100 to move easily on the floor through the casters.

[1-2-2] Arm 104

The arm 104 includes a plurality of links coupled mutually through joints. The arm 104 has at least six degrees of freedom due to rotational motion about rotation axes to be described later. The example illustrated in FIG. 1 indicates an exemplary configuration of six degrees of freedom as described later.

In addition, the arm 104 supports the imaging device 106 (exemplary medical device). The imaging device 106 supported by the arm 104 is movable three-dimensionally. The imaging device 106 after movement is retained in position and posture by the arm 104.

More specifically, the arm 104 includes, for example, a plurality of joints 110a, 110b, 110c, 110d, 110e, and 110f, and a plurality of links 112a, 112b, 112c, 112d, 112e, and 112f coupled through the joints 110a, 110b, 110c, 110d, 110e, and 110f. The respective rotatable ranges of the joints 110a, 110b, 110c, 110d, 110e, and 110f are optionally set, for example, at the design stage or fabrication stage such that the arm 104 achieves desired motion.

That is the medical holding apparatus 100 illustrated in FIG. 1 has six degrees of freedom in movement of the imaging device 106 with six rotation axes (first axis O1, second axis O2, third axis O3, fourth axis O4, fifth axis O5, and sixth axis O6) corresponding to the six joints 110a, 110b, 110c, 110d, 110e, and 110f included in the arm 104. More specifically, the medical holding apparatus 100 illustrated in FIG. 1 has the six degrees of freedom of three degrees of freedom in translation and three degrees of freedom in rotation, in motion.

The first axis O1 is the first rotation axis from the side on which the imaging device 106 is supported, of the arm 104 (side on which the medical device is supported, of the arm, hereinafter, the same applies). The second axis O2 is the second rotation axis from the side on which the imaging device 106 is supported, of the arm 104. The third axis O3 is the third rotation axis from the side on which the imaging device 106 is supported, of the arm 104. The fourth axis O4 is the fourth rotation axis from the side on which the imaging device 106 is supported, of the arm 104. The fifth axis O5 is the fifth rotation axis from the side on which the imaging device 106 is supported, of the arm 104. The sixth axis O6 is the sixth rotation axis from the side on which the imaging device 106 is supported, of the arm 104.

With another expression, the sixth axis O6 is the first rotation axis from the side opposite to the side on which the imaging device 106 is supported, of the arm 104 (side opposite to the side on which the medical device is supported, of the arm, hereinafter, the same applies). The fifth axis O5 is the second rotation axis from the side opposite to the side on which the imaging device 106 is supported, of the arm 104. The fourth axis O4 is the third rotation axis from the side opposite to the side on which the imaging device 106 is supported, of the arm 104. The third axis O3 is the fourth rotation axis from the side opposite to the side on which the imaging device 106 is supported, of the arm 104. The second axis O2 is the fifth rotation axis from the side opposite to the side on which the imaging device 106 is supported, of the arm 104. The first axis O1 is the sixth rotation axis from the side opposite to the side on which the imaging device 106 is supported, of the arm 104.

Three or more joints among the joints 110a, 110b, 110c, 110d, 110e, and 110f included in the arm 104 each are provided with an actuator (not illustrated) and an angular sensor (not illustrated).

The actuator (not illustrated) serves to give the joint an assist force of assisting rotational motion. Each joint provided with the actuator (not illustrated) rotates around the corresponding rotation axis, due to the assist force given by the drive of the actuator (not illustrated). The drive of the actuator (not illustrated) is controlled by, for example, the at least one processor that functions as the control unit to be described later or an external medical control device (not illustrated).

The angular sensor (not illustrated) serves to detect the rotation angle of the rotation axis. Examples of the angular sensor according to the present embodiment include any sensor capable of acquiring the rotation angle at a rotation axis, such as a rotary encoder and an angular rate sensor. Note that the angular sensor (not illustrated) and the actuator (not illustrated) may be an integrated device or may be separated devices.

Examples of the three or more joints each provided with the actuator (not illustrated) and the angular sensor (not illustrated), namely, examples in arrangement of the actuator (not illustrated) and the angular sensor (not illustrated) are as follows: Note that, needless to say, examples in arrangement of the actuator (not illustrated) and the angular sensor (not illustrated) are not limited to the following examples. As an example, in a case where the angular sensor (not illustrated) is disposed at all the joints, the actuator (not illustrated) may be disposed at three or more joints that are part of all the joints.

First example in arrangement: the joints 110a, 110b, and 110c (three joints corresponding to the first rotation axis, the second rotation axis, and the third rotation axis from the side on which the imaging device 106 is supported, of the arm 104, hereinafter, the same applies).

Second example in arrangement: the joints 110d, 110e, and 110f (three joints corresponding to the first rotation axis, the second rotation axis, and the third rotation axis from the side opposite to the side on which the imaging device 106 is supported, of the arm 104, hereinafter, the same applies).

Third example in arrangement: the joints 110a, 110b, 110c, 110d, 110e, and 110f (all the joints).

For example, the joints 110a, 110b, 110c, 110d, 110e, and 110f rotate around the corresponding rotation axes, so that various motions of the arm 104 are achieved, such as extension and retraction (folding) of the arm 104. For example, the rotation axis corresponding to each joint rotates due to either or both application of force responsive to an operation of the operator (e.g., an operation for moving the imaging device 106) and application of the assist force responsive to the drive of the actuator (not illustrated) provided.

At the distal-end portion of the joint 110a (lower-end portion in FIG. 1), the joint 110a supports the imaging device 106 (upper-end portion of the imaging device 106 in FIG. 1) turnably around the rotation axis (first axis O1) parallel to the central axis of the imaging device 106. Here, the medical holding apparatus 100 illustrated in FIG. 1 has the first axis O1 identical to the optical axis of the imaging device 106. In other words, the first axis O1 is identical in axis to the optical axis of the imaging device 106. That is turning the imaging device 106 around the first axis O1 illustrated in FIG. 1 causes the medical imaged image imaged by the imaging device 106, to result in an image changed such that the field of view is rotated. Note that, needless to say, the medical holding apparatus 100 is not limited in configuration to the first axis O1 identical in axis to the optical axis of the imaging device 106.

The link 112a fixedly supports the joint 110a. For example, the link 112a extends in a direction substantially orthogonal to the first axis O1 and is connected with the joint 110b.

The joint 110b supports the link 112a turnably around the rotation axis (second axis O2) orthogonal to the first axis O1. In addition, the joint 110b is connected with the link 112b.

The link 112b fixedly supports the joint 110b. In addition, the link 112b is connected with the joint 110c.

The joint 110c supports the link 112b turnably around the rotation axis (third axis O3) mutually orthogonal to, at least, the second axis O2. In addition, the joint 110c is connected with one end of the link 112c.

Here, turning the distal-end side of the arm 104 (side on which the imaging device 106 is provided) around the second axis O2 and the third axis O3 enables the imaging device 106 to move such that the imaging device 106 rotates. Note that, in a case where turning around the second axis O2 and the third axis O3 is slight, the field of view of the medical imaged image seems to move in plane. In addition, as described above, in the medical holding apparatus 100, turning the imaging device 106 around the first axis O1 causes the field of view of the medical imaged image to rotate.

Therefore, in the medical holding apparatus 100, the first axis O1, the second axis O2, and the third axis O3 (the first rotation axis, the second rotation axis, and the third rotation axis from the side on which the imaging device 106 is supported, of the arm 104) are regarded as rotation axes for tilt motion of the imaging device 106. In addition, the links 112a, 112b, and 112c connected mutually with the joint 110a corresponding to the first axis O1, the joint 110b corresponding to the second axis O2, and the joint 110c corresponding to the third axis O3 serve as a horizontal arm in the arm 104.

The link 112c is connected with the link 112b through the joint 110c and is connected with the link 112d through the joint 110d.

The joint 110d supports the link 112c turnably around the rotation axis (fourth axis O4) orthogonal to the third axis O3. The joint 110d is connected with the link 112d.

The link 112d is connected with the link 112c through the joint 110d and is connected with the link 112e through the joint 110e.

In addition, the link 112d is provided with a counterweight 114. The counterweight 114 makes adjustments in mass and arrangement position so as to cancel the moment in rotation occurring around the fourth axis O4 and the moment in rotation occurring around the fifth axis O5 due to the mass of each constituent element provided closer to the distal-end side of the arm 104 (side on which the imaging device 106 is provided) than the counterweight 114 is.

The joint 110e supports one end of the link 112d turnably around the rotation axis (fifth axis O5) parallel to the fourth axis O4. In addition, the joint 110e is connected with one end of the link 112e.

Here, the fourth axis O4 and the fifth axis O5 are rotation axes enabling the imaging device 106 to move either or both vertically and horizontally. Turning the distal-end side of the arm 104 (side on which the imaging device 106 is provided) around the fourth axis O4 and the fifth axis O5 enables the vertical position and the horizontal position of the horizontal arm to be changed. Thus, the vertical position and the horizontal position of the imaging device 106 supported by the arm 104 can be changed. Therefore, turning the distal-end side of the arm 104 (side on which the imaging device 106 is provided) around the fourth axis O4 and the fifth axis O5 enables change of the distance between the imaging device 106 and a target to be observed, such as the surgical site of a patient.

The one end of the link 112e is connected with the joint 110e and the other end is connected with the joint 110f.

The joint 110f is connected with the link 112e and the link 112f. The joint 110f supports the link 112f turnably around the rotation axis (sixth axis O6) parallel to the vertical direction.

Here, turning the link 112f around the sixth axis O6 causes the entirety of the arm 104 to turn. In addition, as described above, turning the distal-end side of the arm 104 (side on which the imaging device 106 is provided) around the fourth axis O4 and the fifth axis O5 causes one or both of the vertical position and the horizontal position of the horizontal arm, to be changed.

Therefore, in the medical holding apparatus 100, the sixth axis O6, the fifth axis O5, and the fourth axis (the first rotation axis, the second rotation axis, and the third rotation axis from the side opposite to the side on which the imaging device 106 is supported, of the arm 104) serve for large movement of the position of the horizontal arm.

Because the arm 104 has the configuration above, the medical holding apparatus 100 has the six degrees of freedom in movement of the imaging device 106 and additionally functions as a balanced arm with the counterweight 114.

Note that the arm 104 is not limited in configuration to the example given above.

For example, the joints 110a, 110b, 110c, 110d, 110e, and 110f of the arm 104 may be provided with brakes that regulate respective rotations of the joints 110a, 110b, 110c, 110d, 110e, and 110f. Examples of the brakes according to the present embodiment include any type of brake, such as a mechanically driven brake and an electrically driven electromagnetic brake.

The drive of the brakes is controlled by, for example, the at least one processor that functions as the control unit to be described later or the external medical control device (not illustrated). Control of the drive of the brakes causes the operation mode of the arm 104 to be set in the medical holding apparatus 100. Examples of the operation mode of the arm 104 include a fixed mode and a free mode.

Here, the fixed mode according to the present embodiment is, for example, an operation mode in which the imaging device 106 is fixed in position and posture with each rotation axis provided at the arm 104 regulated in rotation by the brake. With the arm 104 in the fixed mode, the motion state of the medical holding apparatus 100 is a fixed state where the imaging device 106 is fixed in position and posture.

In addition, the free mode according to the present embodiment is an operation mode in which each rotation axis provided at the arm 104 is allowed to rotate freely with the brakes released. For example, in the free mode, the imaging device 106 can be adjusted in position and posture by a direct operation of the surgical operator (exemplary operator). Here, the direct operation according to the present embodiment means, for example, an operation in which the surgical operator directly moves the imaging device 106 while grasping the imaging device 106 by hand.

[1-2-3] Imaging Device 106

The imaging device 106 is supported by the arm 104 and images a target to be observed, such as the surgical site of a patient.

For example, the imaging device 106 corresponds in configuration to an electronic-imaging microscope.

As an example, the imaging device 106 includes an optical system and an image sensor. For example, the optical system includes, as optical elements, an objective lens, at least one lens of a zoom lens and a focusing lens, and a mirror. Examples of the image sensor include an image sensor with a complementary metal oxide semiconductor (CMOS) as an imaging element and an image sensor with a charge coupled device (CCD) as an imaging element.

For example, the imaging device 106 may include a Galilean optical system or a Greenough optical system and a plurality of image sensors, so as to function as a so-called stereo camera.

The imaging device 106 is equipped with at least one function among functions that an electronic-imaging microscope unit generally has, such as a zoom function (one or both of an optical zoom function and an electronic zoom function) and an auto focus (AF) function.

In addition, the imaging device 106 may be capable of performing imaging at a so-called high resolution, such as 4K resolution or 8K resolution. In a case where an imaging member 120 is capable of performing imaging at high resolution, the imaging member 120 enables a display device having a display screen that is, for example, a large screen of 50 or more inches to display an image with a predetermined resolution (e.g., Full HD image quality) secured. Thus, improvement is made in visibility to the surgical operator who views the display screen. In addition, in a case where the imaging device 106 is capable of performing imaging at high resolution, even when the imaged image is magnified by the electronic-zoom function and is displayed on the display screen of the display device, the predetermined resolution can be secured. Furthermore, in a case where the predetermined resolution is secured with the electronic zoom function, the performance of the optical zoom function in the imaging device 106 can be saved. Thus, the optical system of the imaging device 106 can be further simplified, so that the imaging device 106 can be made more compact.

In addition, the imaging device 106 may be provided with, for example, various types of operation devices for controlling the operation of the imaging device 106. Examples of the operation devices with which the imaging device 106 is provided include part or all of a zoom switch, a focusing switch, and an operation-mode setting switch.

The zoom switch and the focusing switch are exemplary operation devices for adjusting imaging conditions, in the imaging device 106.

The zoom switch includes, for example, a zoom-in switch for increase in zoom magnification (magnifying power) and a zoom-out switch for decrease in zoom magnification. Operating the zoom switch causes adjustment in zoom magnification, resulting in adjustment in zooming.

The focusing switch includes, for example, a long-distance focusing switch for lengthening the focal length to the target to be observed (subject) and a short-distance focusing switch for shortening the focal length to the target to be observed. Operating the focusing switch causes adjustment in focal length, resulting in adjustment in focusing.

The operation-mode changeover switch is an exemplary operation device for changing the operation mode of the arm 104, in the imaging device 106. Operating the operation-mode changeover switch causes change of the operation mode of the arm 104. As described above, examples of the operation mode of the arm 104 include the fixed mode and the free mode.

An exemplary operation to the operation-mode changeover switch is an operation of pressing down the operation-mode changeover switch. For example, while the surgical operator is pressing down the operation-mode changeover switch, the operation mode of the arm 104 is in the free mode. When the surgical operator has not pressed down the operation-mode changeover switch, the operation mode of the arm 104 is in the fixed mode.

For example, an image signal (image data) generated on the basis of imaging in the imaging device 106 is subjected to image processing by the at least one processor that functions as the control unit to be described later. Examples of the image processing according to the present embodiment include at least one piece of processing among various types of processing, such as gamma correction, adjustment of white balance, magnification and reduction of an image according to the electronic zoom function, and inter-pixel correction. Note that the image processing according to the present embodiment may be performed by the external medical control device (not illustrated).

The medical holding apparatus 100 transmits, for example, a display control signal and the image signal subjected to the image processing as above to an external display device.

After the display control signal and the image signal are transmitted to the display device, a medical imaged image in which the target to be observed is imaged (e.g., an imaged image in which the surgical site is imaged) is displayed on the display screen of the display device at a predetermined magnification magnified or reduced by one or both of the optical zoom function and the electronic zoom function.

The medical holding apparatus 100 has, for example, the hardware configuration given with reference to FIG. 1.

Note that the medical holding apparatus according to the present embodiment is not limited in hardware configuration to the configuration given with reference to FIG. 1.

For example, the medical holding apparatus according to the present embodiment may have the arm 104 to be directly mounted on, for example, the ceiling or a wall face of a surgery, without the base 102. For example, in a case where the arm 104 is mounted on the ceiling, the medical holding apparatus according to the present embodiment has the arm 104 extending downward from the ceiling.

In addition, FIG. 1 exemplifies that the arm 104 has the six degrees of freedom in drive of the imaging device 106. However, the arm 104 is not limited in configuration to the six degrees of freedom for the degree of freedom in drive of the imaging device 106. For example, the arm 104 needs at least to have six or more degrees of freedom as described above. The number of joints and links, the arrangement thereof, and the directions of driving axes of joints can be appropriately set such that the arm 104 has six or more degrees of freedom.

In addition, the example in which the various types of operation devices for controlling the operation of the imaging device 106 are provided at the imaging device 106, has been given above. However, part or all of the operation devices are not necessarily provided at the imaging device 106. As an example, the various types of operation devices for controlling the operation of the imaging device 106 may be provided at a part different from the imaging device 106 included in the medical holding apparatus according to the present embodiment. In addition, as another example, the various types of operation devices for controlling the operation of the imaging device 106 may be any external operation device, such as a foot switch and a remote controller.

In addition, the imaging device 106 may be capable of performing switching between a plurality of observation modes. Examples of the observation modes according to the present embodiment include an observation mode in which imaging is performed with natural light, an observation mode in which imaging is performed with particular light, and an observation mode in which imaging is performed with an image-enhanced observation technique, such as narrow band imaging (NBI). The particular light according to the present embodiment is, for example, light in a specified wavelength band, such as light in a near-infrared wavelength band or light in a fluorescence wavelength band for fluorescent observation with 5-aminolevulinic acid (5-ALA).

An exemplary configuration of the imaging device 106 capable of performing switching between the plurality of observation modes" includes: a filter that allows light in the specified wavelength band to pass therethrough and does not allow light in the other wavelength bands to pass therethrough; and a movement mechanism of selectively disposing the filter on the optical path". Examples of the specified wavelength band that passes through the filter according to the present embodiment include the near-infrared wavelength band (e.g., the wavelength band of from approximately 0.7 to 2.5 [μm]), the fluorescence wavelength band for fluorescent observation with 5-ALA (e.g., the wavelength band of from approximately 0.6 to 0.65 [μm]), and the fluorescence wavelength band of Indocyanine green (ICG) (e.g., the wavelength band of from approximately 0.82 to 0.85 [μm]).

Note that the imaging device 106 may be provided with a plurality of filters different in wavelength band for transmission. In addition, the example in which the filter is disposed on the optical path such that imaging is performed with light in the specified wavelength band, has been given above. However, needless to say, the imaging device 106 that performs imaging with light in the specified wavelength band, is not limited in configuration to the example given above.

Furthermore, the medical holding apparatus according to the present embodiment may have a hardware configuration corresponding to an applied example.

Figure 2:
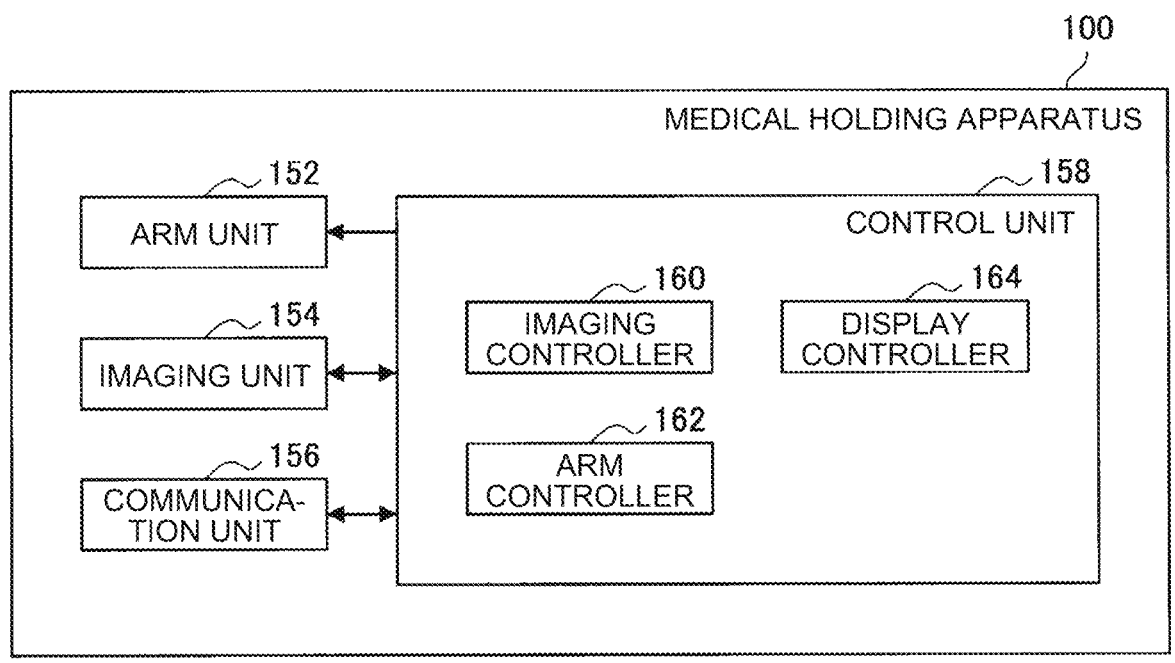
FIG. 2 is a functional block diagram illustrating the exemplary configuration of the medical holding apparatus according to the present embodiment.

Next, the medical holding apparatus 100 illustrated in FIG. 1 will be described with functional blocks. FIG. 2 is a functional block diagram illustrating the exemplary configuration of the medical holding apparatus 100 according to the present embodiment, in which exemplary functional blocks of the medical holding apparatus 100 that functions as the electronic-imaging medical observation apparatus are illustrated.

The medical holding apparatus 100 includes, for example, an arm unit 152, an imaging unit 154, a communication unit 156, and a control unit 158.

The arm unit 152 including the arm 104 supports the imaging device 106 included in the imaging unit 154.

The imaging unit 154 including the imaging device 106 images a target to be observed. Imaging in the imaging unit 154 is controlled by, for example, the control unit 158.

The communication unit 156 that is communication means included in the medical holding apparatus 100, serves to communicate with an external device, such as a display device, by wireless or by wire. The communication unit 156 includes, for example, the communication device (not illustrated) described above. Communication in the communication unit 156 is controlled by, for example, the control unit 158.

The control unit 158 including, for example, the at least one processor (not illustrated) described above serves to control the entirety of the medical holding apparatus 100. In addition, the control unit 158 serves to perform, in a leadership manner, processing according to the control method to be described later. Note that the processing according to the control method in the control unit 158 may be performed in a decentralized manner by a plurality of processing circuits (e.g., a plurality of processors).

More specifically, the control unit 158 includes, for example, an imaging controller 160, an arm controller 162, and a display controller 164.

The imaging controller 160 controls the imaging device 106 included in the imaging unit 154. The control of the imaging device 106 is, for example, control of at least one function inclusive of at least a zoom function (optical zoom function and electronic zoom function) among functions that an electronic-imaging microscope unit generally has, such as control of an AF function.

The arm controller 162 serves to perform the processing according to the control method to be described later and controls the motion of the arm 104 included in the arm unit 152. For example, the arm controller 162 "applies a control signal of controlling driving to the at least three joints each provided with the actuator (not illustrated)", to control the motion of the arm 104. Exemplary processing according to the control method according to the present embodiment will be described later.

For example, the display controller 164 sends the display control signal and the image signal to the communication device (not illustrated) included in the communication unit 156. Then, the communication device (not illustrated) transmits the display control signal and the image signal to the display device, so that display in the display device is controlled. Note that communication in the communication unit 156 may be controlled by a communication controller (not illustrated) included in the control unit 158.

The control unit 158 with, for example, the arm controller 162 serves to perform, in a leadership manner, the processing according to the control method according to the present embodiment. In addition, the control unit 158 with, for example, the imaging controller 160, the arm controller 162, and the display controller 164 serves to control the entirety of the medical holding apparatus 100 that functions as the electronic-imaging medical observation apparatus.

Note that the control unit 158 is not limited in functional configuration to the example illustrated in FIG. 2.

For example, the control unit 158 can have any configuration corresponding to division of the functions included in the medical holding apparatus 100, such as a configuration corresponding to division of the processing according to the control method according to the present embodiment.

For example, with the configuration illustrated in FIG. 2, the medical holding apparatus 100 performs the processing according to the control method according to the present embodiment to be described later.

Note that the medical holding apparatus according to the present embodiment is not limited in functional configuration to the configuration illustrated in FIG. 2.

For example, the medical holding apparatus according to the present embodiment can include part or all of the imaging controller 160, the arm controller 162, and the display controller 164 illustrated in FIG. 2, separately from the control unit 158 (e.g., achievement with a different processing circuit).

In addition, for achievement of the processing according to the control method according to the present embodiment, the medical holding apparatus according to the present embodiment is not limited in functional configuration to the configuration illustrated in FIG. 2. For example, the medical holding apparatus according to the present embodiment can have a functional configuration corresponding to division of the processing according to the control method according to the present embodiment.

In addition, for example, in a case where performed is communication with an external device through an external communication device similar in function and configuration to the communication unit 156, the medical holding apparatus according to the present embodiment does not necessarily have the communication unit 156.

In addition, the medical holding apparatus according to the present embodiment may have a functional configuration corresponding to an applied example. As an example, in a case where the medical holding apparatus according to the present embodiment is an optical medical observation apparatus or an endoscope holder, the medical holding apparatus according to the present embodiment does not necessarily have the imaging unit 154 and the imaging controller 160 illustrated in FIG. 2.

[2] Control Method According to Present Embodiment

Next, the control method according to the present embodiment will be described. An exemplary case where the medical holding apparatus 100 (more specifically, for example, the arm controller 162 in the control unit 158 included in the medical holding apparatus 100) performs the processing according to the control method according to the present embodiment, will be given below.

[2-1] Outline of Control Method According to Present Embodiment

As described above, in a case where the amount of force in operation necessary "when an operator moves a medical device supported by an arm" (hereinafter, simply referred to as the "amount of force in operation") varies significantly depending on the posture of the arm, the operator is likely to fatigue in operation.

The amount of force in operation is determined by the amount of force at each rotation axis of the arm and depending on which of the rotation axes of the arm moves. The amount of force at each rotation axis of the arm is expressed by, for example, Mathematical Expression 1 below. In addition, the amount of force in operation is expressed by, for example, Mathematical Expression 2 below. Hereinafter, the "inertial force from the distal-end side of the arm to a rotation axis" indicated in Mathematical Expression 1 below is simply referred to as the "inertial force to a rotation axis".

The individual amount of force in operation at each rotation axis={the weight in rotation at the rotation axis corresponding to the joint+the inertial force (total weight) from the distal-end side of the arm (side on which the medical device is supported) to the rotation axis}×the direct distance from the operation position to the rotation axis (Mathematical Expression 1)

The total amount of force in operation=the sum total of the amounts of force in operation at rotation axes that move in conjunction with an operation (Mathematical Expression 2)

Here, a rotation axis that moves due to an operation of the operator, among the rotation axes of the arm, is determined by the posture of the arm and the direction in which the operator moves the medical device. In the medical holding apparatus, the number of rotation axes that move in conjunction with an operation varies depending on the way the operator moves the medical device. Thus, the amount of force in operation is not constant, resulting in non-uniformity.

However, an existing medical holding apparatus has not taken account of uniforming the amount of force in operation, and thus are incapable of uniforming the amount of force in operation. Therefore, an operator who uses such an existing medical holding apparatus is likely to feel fatigued in operation.

A case where the amount of force in operation varies in a medical holding apparatus will be described below with the configuration of the medical holding apparatus 100 described with reference to FIG. 1 as an example.

Figure 3:
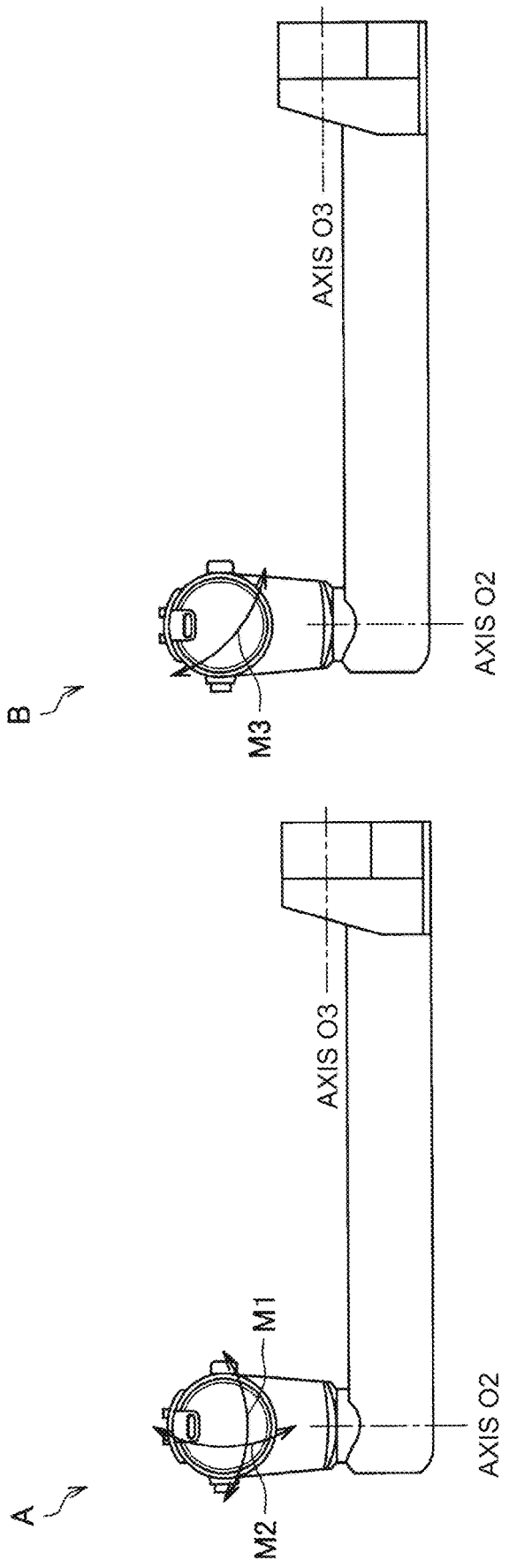
FIG. 3 is an explanatory view for describing a first case where the amount of force in operation varies in the medical holding apparatus.

FIG. 3 is an explanatory view for describing a first case where the amount of force in operation varies in the medical holding apparatus. A of FIGS. 3 and B of FIG. 3 illustrate exemplary cases where the rotation axes O2 and O3 each are a rotation axis that moves in conjunction with an operation. "M1", "M2", and "M3" in FIG. 3 each indicate a motion when the operator moves the imaging device 106 supported by the arm 104.

For example, in a case where the imaging device 106 moves as indicated with M1 of FIG. 3, only the rotation axis O2 turns. Therefore, in a case where the imaging device 106 moves as indicated with M1 of FIG. 3, from Mathematical Expression 1 above and Mathematical Expression 2 above, "the amount of force at the rotation axis O2+the inertial force to the rotation axis O2" results in the weight to the operator in operation, namely, the amount of force in operation.

In addition, for example, in a case where the imaging device 106 moves as indicated with M2 of FIG. 3, only the rotation axis O3 turns. Therefore, in a case where the imaging device 106 moves as indicated with M2 of FIG. 3, from Mathematical Expression 1 above and Mathematical Expression 2 above, "the amount of force at the rotation axis O3+the inertial force to the rotation axis O3" results in the amount of force in operation.

Here, in a case where only the rotation axis O2 turns or in a case where only the rotation axis O3 turns, the arm 104 can be designed such that the amount of force at the rotation axis O2 and the amount of force at the rotation axis O3 are identical.

However, for example, in a case where the imaging device 106 moves as indicated with M3 of FIG. 3, both of the rotation axis O2 and the rotation axis O3 turn. Therefore, in a case where the imaging device 106 moves as indicated with M3 of FIG. 3, from Mathematical Expression 1 above and Mathematical Expression 2 above, "the amount of force at the rotation axis O2+the amount of force at the rotation axis O3+the inertial force to the rotation axis O3" results in the amount of force in operation.

Here, in a case where the imaging device 106 moves as indicated with M3 of FIG. 3, the amount of force at the rotation axis O2 and the amount of force at the rotation axis O3 are applied. Thus, it is physically impossible that the case is identical in motion and the amount of force to a case where only one of the rotation axis O2 and the rotation axis O3 turns.

Figure 4:
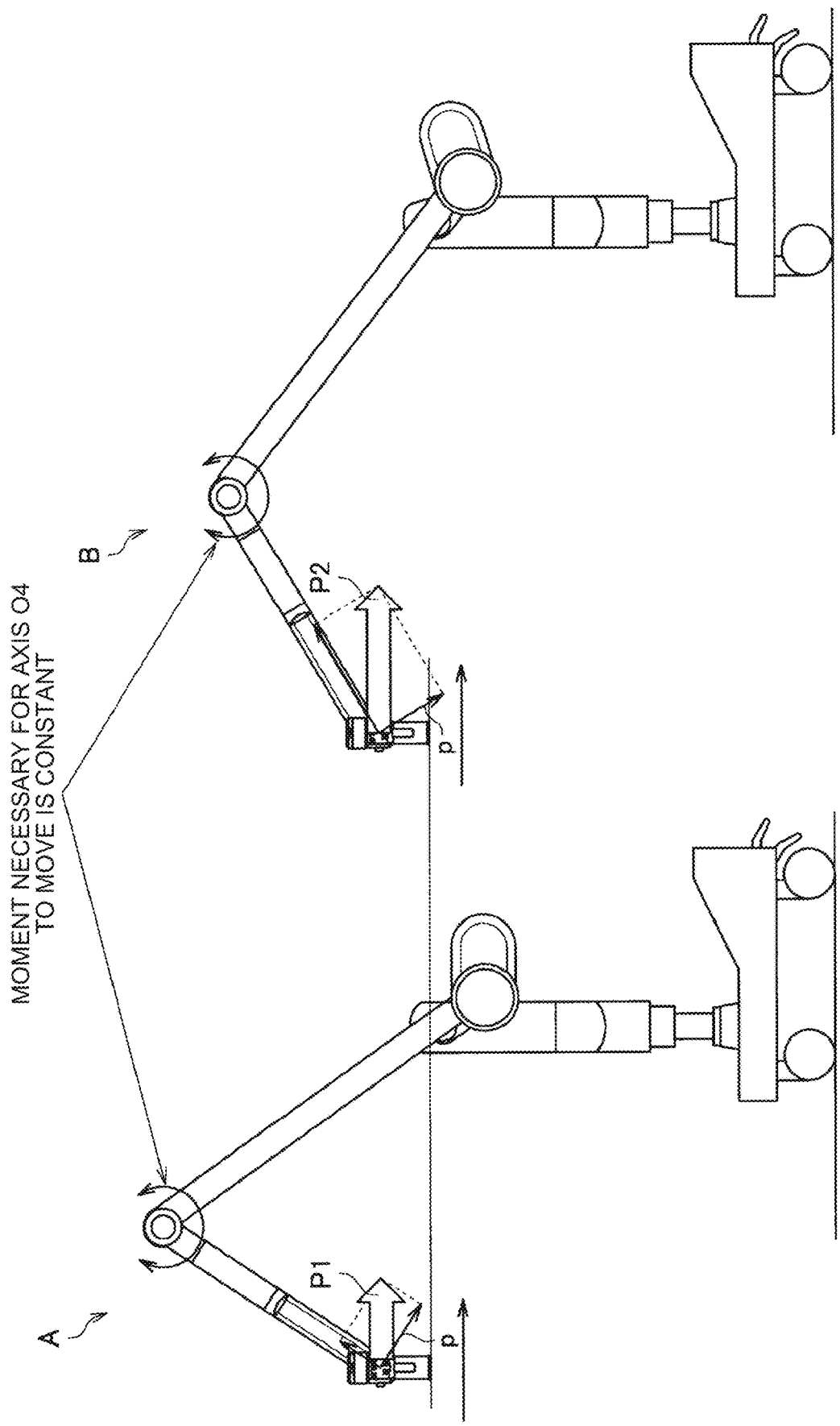
FIG. 4 is an explanatory view for describing a second case where the amount of force in operation varies in the medical holding apparatus.

FIG. 4 is an explanatory view for describing a second case where the amount of force in operation varies in the medical holding apparatus. A of FIGS. 4 and B of FIG. 4 illustrate exemplary cases where "the operation axes O4 and O5 each are a rotation axis that moves in conjunction with an operation when the posture of the arm 104 varies". "P1" and "P2" in FIG. 4 each indicate the level of the amount of force in operation in vector representation.

Because the moment of inertia necessary for the rotation axis O4 to move is constant, force indicated with the vector p of FIG. 4 (force to the imaging device 106 for generation of the moment of inertia) is constant. However, as indicated with P1 and P2 of FIG. 4, in a case where the posture of the arm 104 varies, the amount of force in operation necessary for generation of the force indicated with the vector p varies. That is, as indicated with P1 and P2 of FIG. 4, even when the imaging device 106 moves by the same distance in the same direction at the same height, the amount of force in operation varies depending on the posture of the arm 104. In the example of FIG. 4, even in a case where the imaging device 106 moves in the same manner, a larger force is required for the posture of the arm 104 illustrated in B of FIG. 4 than for the posture of the arm 104 illustrated in A of FIG. 4.

Figure 5:
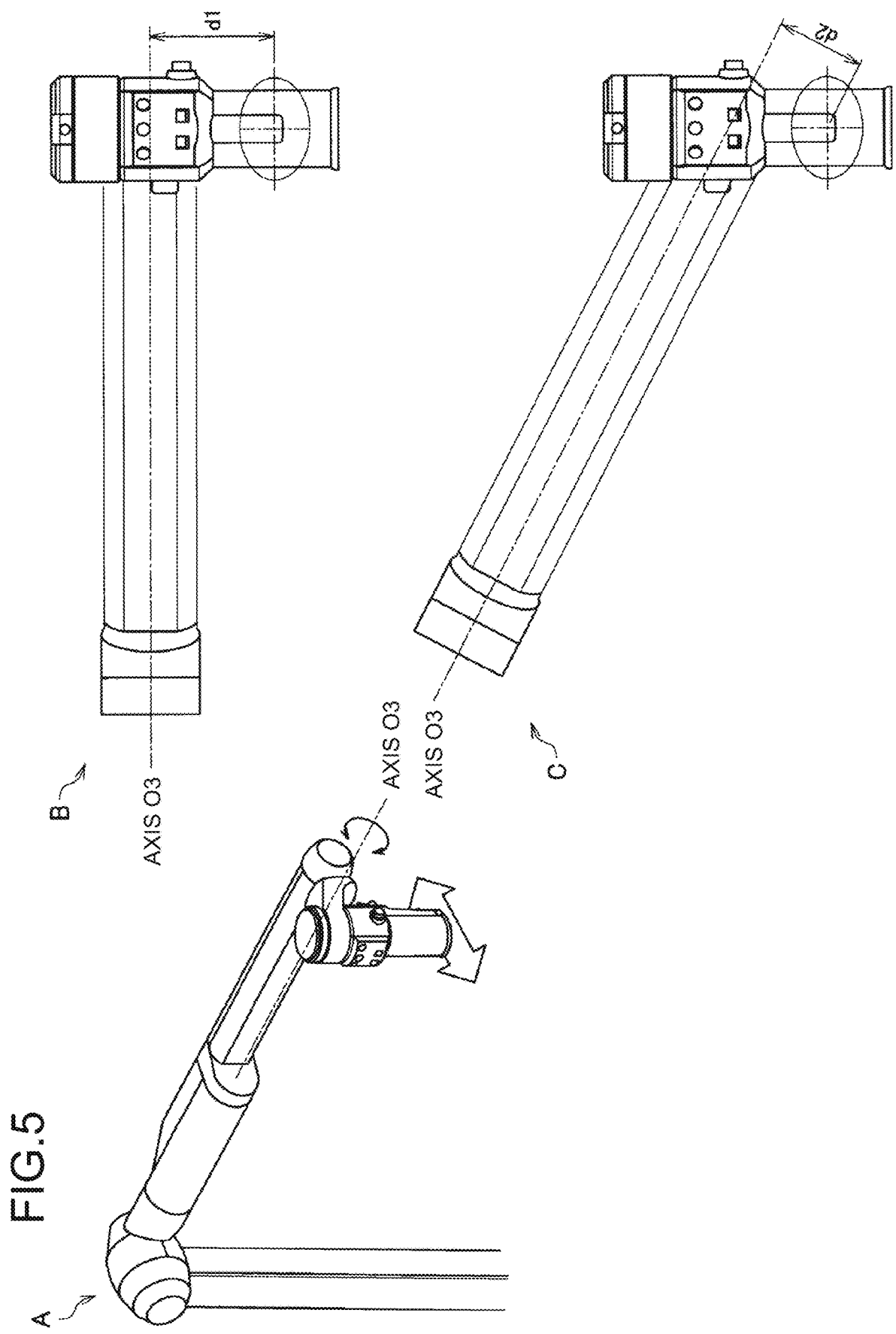
FIG. 5 is an explanatory view for describing a third case where the amount of force in operation varies in the medical holding apparatus.

FIG. 5 is an explanatory view for describing a third case where the amount of force in operation varies in the medical holding apparatus. A of FIG. 5, B of FIGS. 5, and C of FIG. 5 illustrate exemplary cases where "the rotation axis O3 is a rotation axis that moves in conjunction with an operation when the posture of the arm 104 varies". "d1" and "d2" in FIG. 5 each indicate the distance between the rotation axis O3 and the operation position of the imaging device 106.

From Mathematical Expression 1 above and Mathematical Expression 2 above, in a case where the distance between the rotation axis O3 and the operation position of the imaging device 106 varies, the amount of force in operation varies.

Like the cases given with reference to FIGS. 3 to 5, there are various cases where the amount of force in operation varies in medical holding apparatus. Note that, needless to say, the case where the amount of force in operation varies in the medical holding apparatus is not limited to the cases given with reference to FIGS. 3 to 5.

Thus, the medical holding apparatus 100 controls the motion of the arm 104 such that the amount of force in operation necessary when the operator moves the imaging device 106 (exemplary medical device, hereinafter, the same applies) supported by the arm 104 remains in a predetermined range.

Here, in a case where the pitch between each rotation axis, namely, the length of each link is known, acquisition of the angle of each rotation axis enables specification of the posture of the arm 104 at the time (or estimation of the posture of the arm 104). Note that the method of specifying the posture of the arm 104 (or the method of estimating the posture of the arm 104) is not limited to the example given above. Thus, the medical holding apparatus 100 may specify the posture of the arm 104 with any method enabling specification of the posture of the arm 104.

In addition, on the basis of the rotation angles of the rotation axes detected by the angular sensors (not illustrated) provided at the at least three joints of the arm 104, which direction the operator wants to move the imaging device 106 in can be specified.

Therefore, from Mathematical Expression 1 above and Mathematical Expression 2 above, the amount of force in operation necessary when the operator moves the imaging device 106 can be calculated.

The medical holding apparatus 100 controls the respective assist forces of the actuators (not illustrated) provided at the at least three joints of the arm 104 such that the amount of force in operation remains in the predetermined range. Controlling the respective assist forces of the actuators (not illustrated) such that the amount of force in operation remains in the predetermined range, causes the amount of force in operation to be adjusted by the assist forces. As a result, the amount of force in operation can be uniformed.

More specifically, the medical holding apparatus 100 controls the respective assist forces of the actuators (not illustrated), for example, such that the amount of force in operation remains in an allowable range including a set value having been set.

The allowable range including the set value is, for example, a range with a lower-limit value that is "the set value−the set value×X [%]" (X is an integer of 0 or more) and an upper-limit value that is "the set value+the set value×Y [%]" (Y is an integer of 0 or more). That is the predetermined range according to the present embodiment is defined by, for example, the set value, the lower-limit value, and the upper-limit value. The allowable range according to the present embodiment may include the upper-limit value and the lower-limit value or may exclude one or both of the upper-limit value and the lower-limit value.

For example, the upper-limit value and the lower-limit value each are set to a fixed value, in accordance with the accuracy of control according to the control method, at any stage of the medical holding apparatus 100, such as a design stage or an initial setting stage. As an example, in a case where a higher accuracy of control is required, the value of X and the value of Y are set at, for example, 20[%] or less. In addition, as another example, for improvement in operability with reduction of the fatigue of a user, the value of X and the value of Y are preferably set at, for example, 40[%] or less. Note that, needless to say, exemplary upper-limit and lower-limit values defining the allowable range according to the present embodiment are not limited to the examples given above.

Note that the upper-limit value and the lower-limit value each are not limited to the fixed value. For example, similarly to the set value to be described later, the upper-limit value and the lower-limit value each may be manually changed on the basis of an operation of, for example, the operator, or may be automatically changed in accordance with the operation of the medical device supported by the arm 104.

In addition, needless to say, the upper-limit value and the lower-limit value each are not limited to definition in percentage like the examples given above.

As the set value increases, movement of the imaging device 106 requires a larger amount of force in operation. Thus, for example, a larger set value is suitable for slight movement of the imaging device 106. In addition, as the set value decreases, movement of the imaging device 106 requires a smaller amount of force in operation. Thus, for example, a smaller set value is suitable for large movement of the imaging device 106.

Here, the set value according to the present embodiment is, for example, a preset fixed value.

In addition, the set value according to the present embodiment may be a variable value that is changeable. For example, the set value may be manually changed on the basis of an operation of, for example, the operator or may be automatically changed in accordance with the operation of the medical device supported by the arm 104.

Examples of the case where the set value is manually changed on the basis of an operation include an example in which the surgical operator selects a preferable set value to set the set value (example in which the set value is directly set) and an example in which the surgical operator selects a procedure to set the set value corresponding to the procedure (example in which the set value is indirectly set).

In addition, examples of the case where the set value is automatically changed in accordance with the operation of the medical device include an example in which, in conjunction with the value of zoom/focusing of the imaging device 106, the set value corresponding to the value of zoom/focusing is set, and an example in which the set value is changed in a case where the field of view of the imaging device 106 deviates from a predetermined range (e.g., a case where the surgical site is out of the medical imaged image). For example, in a case where the imaging device 106 is in magnified view, a large set value is set, so that an operation of moving the imaging device 106 slightly is allowed. In addition, for example, in a case where the imaging device 106 is in wide view, a small set value is set, so that an operation of moving the imaging device 106 largely with a smaller amount of force in operation is allowed. In addition, for example, a larger set value is set in a case where the field of view of the imaging device 106 deviates from the predetermined range, so that deviation of the field of view during surgery can be reduced.

For example, as above, the medical holding apparatus 100 controls the motion of the arm 104 such that the amount of force in operation remains in the predetermined range. Thus, the operator can move the imaging device 106 with uniform force, regardless of the way of moving the imaging device 106.

Therefore, the operator is less likely to fatigue in operation, so that the medical holding apparatus 100 can achieve improvement in operability for the operator.

[2-2] Processing according to Control Method according to Present Embodiment

Next, the processing according to the control method according to the present embodiment will be described more specifically.

As described above, the medical holding apparatus 100 controls the respective assist forces of the actuators (not illustrated) provided at the three or more joints, for example, such that the amount of force in operation is identical to the set value, resulting in uniformity of the amount of force in operation.

For example, in a case where the joints 110*a*, 110*b*, and 110*c* each are provided with the actuator (not illustrated) (first example in arrangement above), the rotation axes O1, O2, and O3 corresponding to the joints 110*a*, 110*b*, and 110*c*, respectively, are rotation axes for tilt motion of the imaging device 106. In addition, the links 112*a*, 112*b*, and 112*c* connected mutually with the joints 110*a*, 110*b*, and 110*c* serve as the horizontal arm in the arm 104. In a case where the rotation axes for tilt motion of the imaging device 106 turn, the object that moves is small, resulting in a small moment of inertia.

Therefore, in the case where the joints 110*a*, 110*b*, and 110*c* each are provided with the actuator (not illustrated) (first example in arrangement above), the medical holding apparatus 100 controls the respective assist forces of the actuators (not illustrated) such that the amount of force in operation is larger than an amount of force in operation in a case where no control is performed.

That is, in the case where the joints 110*a*, 110*b*, and 110*c* each are provided with the actuator (not illustrated) (first example in arrangement above), the set value is set to a value larger than the amount of force in operation necessary in the case where no control is performed. As a specific example of the set value, in the case where the joints 110*a*, 110*b*, and 110*c* each are provided with the actuator (not illustrated) (first example in arrangement above), the set value is set so as to be identical to the amount of force in operation necessary in a case where the rotation axes O4, O5, and O6 corresponding to the joints 110*d*, 110*e*, and 110*f*, respectively, turn. Note that, needless to say, an exemplary set value in the case where the joints 110*a*, 110*b*, and 110*c* each are provided with the actuator (not illustrated) (first example in arrangement above) is not limited to the example given above.

In addition, for example, in a case where the joints 110*d*, 110*e*, and 110*f* each are provided with the actuator (not illustrated) (second example in arrangement above), the rotation axes O4, O5, and O6 corresponding to the joints 110*d*, 110*e*, and 110*f*, respectively, serve for large movement of the position of the horizontal arm. In a case where the rotation axes for large movement of the position of the horizontal arm turn, the object that moves is large, resulting in a large moment of inertia.

Therefore, in the case where the joints 110*d*, 110*e*, and 110*f* each are provided with the actuator (not illustrated) (second example in arrangement above), the medical holding apparatus 100 controls the respective assist forces of the actuators (not illustrated) such that the amount of force in operation is smaller than an amount of force in operation in a case where no control is performed.

That is, in the case where the joints 110*d*, 110*e*, and 110*f* each are provided with the actuator (not illustrated) (second example in arrangement above), the set value is set to a value smaller than the amount of force in operation necessary in the case where no control is performed. As a specific example of the set value, in the case where the joints 110*d*, 110*e*, and 110*f* each are provided with the actuator (not illustrated) (second example in arrangement above), the set value is set so as to be identical to the amount of force in operation necessary in a case where the rotation axes O1, O2, and O3 corresponding to the joints 110*a*, 110*b*, and 110*c*, respectively, turn. Note that, needless to say, an exemplary set value in the case where the joints 110*d*, 110*e*, and 110*f* each are provided with the actuator (not illustrated) (second example in arrangement above) is not limited to the example given above.

For example, in a case where the joints 110*a*, 110*b*, 110*c*, 110*d*, 110*e*, and 110*f* each are provided with the actuator (not illustrated) (third example in arrangement above), the respective assist forces of the actuators (not illustrated) are controlled such that the amount of force in operation remains in the predetermined range even in a case where any rotation axis of the rotation axes O1, O2, O3, O4, O5, and O6 corresponding to the joints 110*a*, 110*b*, 110*c*, 110*d*, 110*e*, and 110*f*, respectively, turns.

Exemplary processing according to the control method according to the present embodiment will be described below with exemplification of "the cases where the rotation axes O1 and O2 each are a rotation axis that moves in conjunction with an operation" given with reference to FIG. 3. Note that, even in any of cases inclusive of the other cases exemplified with reference to FIGS. 4 and 5, similarly to the exemplary processing according to the control method exemplified below, the respective assist forces of the actuators (not illustrated) can be acquired.

Figure 6:
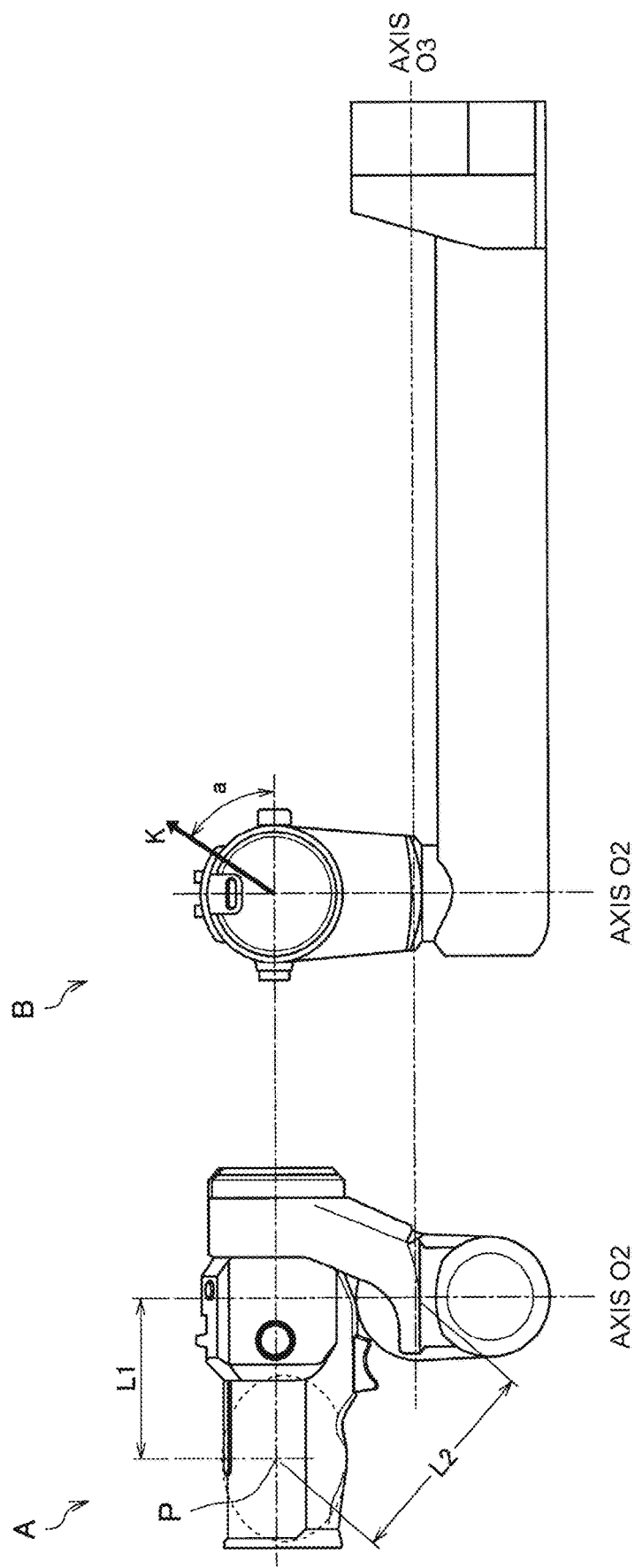
FIG. 6 is an explanatory view for describing exemplary processing according to a control method according to the present embodiment.

FIG. 6 is an explanatory view for describing the exemplary processing according to the control method according to the present embodiment. "P" in FIG. 6 indicates the central position of the imaging device 106. The central position corresponds to the operation position of the imaging device 106. "L1" in FIG. 6 indicates the distance between the rotation axis O1 and the operation position of the imaging device 106. "L2" in FIG. 6 indicates the distance between the rotation axis O2 and the operation position of the imaging device 106. "K" in FIG. 6 indicates the level of the amount of force in operation in vector representation. "a" in FIG. 6 indicates the angle corresponding to the direction of an operation.

The amount of force in operation K has a value corresponding to the allowable range including the set value, and does not depend on the value of angle a. In addition, the component of the amount of force in operation K in the example illustrated in FIG. 6 can be resolved into the component of rotating the rotation axis O2 ("K×sin a") and the component of rotating the rotation axis O1 ("K×cos a") as indicated in Mathematical Expression 3 below. Here, Mathematical Expression 3 below is an expression of components of force, and the value of the amount of force in operation K is a known value corresponding to the set value.

$$K = \sqrt{(K \times \sin a)^2 + (K \times \cos a)^2} \quad \text{(Mathematical Expression 3)}$$

In addition, the component of rotating the rotation axis O2 is expressed by Mathematical Expression 4 below. "T2" in Mathematical Expression 4 below represents the moment at the rotation axis O2, and "t2" in Mathematical Expression 4 below represents the assist force that the actuator (not illustrated) provided at the rotation axis O2 gives the rotation axis O2. That is Mathematical Expression 4 below is an expression of moment.

$$K \times \sin a = \frac{(T2 + t2)}{L2} \quad \text{(Mathmematical Expression 4)}$$

In addition, the component of rotating the rotation axis O1 is expressed by Mathematical Expression 5 below. "T1" in Mathematical Expression 5 below represents the moment at the rotation axis O1, and "t1" in Mathematical Expression 5 below represents the assist force that the actuator (not illustrated) provided at the rotation axis O1 gives the rotation axis O1. That is Mathematical Expression 5 below is an expression of moment.

$$K \times \cos a = \frac{(T1 + t1)}{L1} \quad \text{(Mathmematical Expression 5)}$$

Mathematical Expression 4 above and Mathematical Expression 5 above are substituted into Mathematical Expression 3 above, so that the relationship between the assist force t1 of the actuator (not illustrated) provided at the rotation axis O1 and the assist force t2 of the actuator (not illustrated) provided at the rotation axis O2 is expressed by Mathematical Expression 6 below.

$$K = \sqrt{\left(\frac{T2+t2}{L2}\right)^2 + \left(\frac{T1+t1}{L1}\right)^2} \quad \text{(Mathematical Expression 6)}$$

Here, the value of the amount of force in operation K is a known value corresponding to the allowable range including the set value. Therefore, from Mathematical Expression 6 above, the medical holding apparatus 100 can acquire the assist force t1 of the actuator (not illustrated) provided at the rotation axis O1 and the assist force t2 of the actuator (not illustrated) provided at the rotation axis O2 such that the amount of force in operation K remains in the predetermined range.

The medical holding apparatus 100 operates the actuator (not illustrated) provided at the rotation axis O1 such that the acquired assist force t1 is applied to the rotation axis O1, and operates the actuator (not illustrated) provided at the rotation axis O2 such that the acquired assist force t2 is applied to the rotation axis O2. As above, the medical holding apparatus 100 controls the respective assist forces of the actuators (not illustrated), so that the amount of force in operation is adjusted so as to remain in the predetermined range. Thus, the operator can make an operation in any direction with substantially uniform force in operation.

Therefore, the medical holding apparatus 100 can achieve improvement in operability for the operator.

[3] Exemplary Effects Due to Use of Medical Holding Apparatus According to Present Embodiment Use of the medical holding apparatus according to the present embodiment produces, for example, the following effects. Note that, needless to say, effects due to use of the medical holding apparatus according to the present embodiment are not limited to the examples given below.

The amount of force in operation can be substantially uniformed to an operation of the operator, and thus fatigue due to operation can be reduced.

The operation of the medical device supported by the arm is made in conjunction with the amount of force in operation, such as setting the set value conjunct with the value of zoom/focusing of the imaging device 106, so that the amount of force in operation can be dynamically changed in accordance with the operation of the medical device.

The amount of force in operation can be manually changed in accordance with the preference of the surgical operator or the procedure.

The amount of force in operation is increased in conjunction with deviation of the field of view of the imaging device 106 from the predetermined range, so that deviation of the field of view during surgery can be reduced.

Like the first example in arrangement above and the second example in arrangement above, a case where the actuator (not illustrated) is disposed at part of the joints included in the arm is approximately similar in effect to a case where the actuator (not illustrated) is disposed at all the joints.

Program According to Present Embodiment

A program causing a computer system to function as the medical holding apparatus according to the present embodiment (or the control device according to the present embodiment) (e.g., a program enabling performance of the processing according to the control method according to the present embodiment) is executed by, for example, a processor in the computer system, so that improvement in operability for the operator can be achieved. Here, examples of the computer system according to the present embodiment include a single computer and a plurality of computers. The computer system according to the present embodiment performs a flow of processing according to the control method according to the present embodiment.

In addition, the program causing the computer system to function as the medical holding apparatus according to the present embodiment (or the control device according to the present embodiment) is executed by, for example, the processor in the computer system, so that the effect due to display achieved by the processing according to the control method according to the present embodiment described above can be produced.

The preferred embodiment of the present disclosure has been described in detail above with reference to the accompanying drawings. The technical scope of the present disclosure is not limited to the embodiment. It is obvious that a person skilled in the technical field of the present disclosure conceives various alterations or modifications without departing from the scope of the technical idea in the claims. Thus, it is rightfully understood that such alterations or modifications belong to the technical scope.

The example in which provided is the program (computer program) causing the computer system to function as the medical holding apparatus according to the present embodiment, has been given above. According to the present embodiment, a recording medium storing the program can be further provided.

The configurations described above are exemplary for the present embodiment, and rightfully belong to the technical scope of the present disclosure.

In addition, the effects in the present specification are just explanatory or exemplary, and thus are not limitative. That is the technology according to the present disclosure may produce, in addition to the effects or instead of the effects, other effects obvious to a person skilled in the art from the present specification.

Note that the following configurations belong to the technical scope of the present disclosure.

(1)
A medical holding apparatus including:
an arm including a plurality of links mutually coupled through one of joints, the arm having at least six degrees of freedom due to rotational motion about a rotation axis, the arm being configured to function as a balanced arm with a counterweight and support a medical device; and
an arm controller configured to control motion of the arm, wherein
at least three of the joints in the arm each are provided with an angular sensor that detects a rotation angle of the rotation axis and an actuator that gives the joint an assist force of assisting the rotational motion, and
the arm controller controls, based on respective detected results of the angular sensors, the respective assist forces of the actuators such that an amount of force in operation necessary when an operator moves the medical device supported by the arm remains in a predetermined range.

(2)
The medical holding apparatus according to (1), wherein the arm controller controls the respective assist forces of the actuators such that the amount of force in operation remains in an allowable range including a set value having been set.

(3)
The medical holding apparatus according to (1) or (2), wherein the joints each provided with the angular sensor and the actuator in the arm include three number of the joints corresponding to a rotation axis that is first, a rotation axis that is second, and a rotation axis that is third from a side on which the medical device is supported, of the arm.

(4)
The medical holding apparatus according to (3), wherein the arm controller controls the respective assist forces of the actuators such that the amount of force in operation is larger than an amount of force in operation in a case where no control is performed.

(5)
The medical holding apparatus according to (1) or (2), wherein the joints each provided with the angular sensor and the actuator in the arm include three number of the joints corresponding to a rotation axis that is first, a rotation axis that is second, and a rotation axis that is third from a side opposite to a side on which the medical device is supported, of the arm.

(6)
The medical holding apparatus according to (5), wherein the arm controller controls the respective assist forces of the actuators such that the amount of force in operation is smaller than an amount of force in operation in a case where no control is performed.

(7)
The medical holding apparatus according to (1) or (2), wherein the joints each provided with the angular sensor and the actuator in the arm include all the joints.

(8)
The medical holding apparatus according to any one of (1) to (7), further comprising: the medical device supported by the arm.

(9)
The medical holding apparatus according to (8), wherein the medical device includes an imaging device that images a target to be observed.

REFERENCE SIGNS LIST

100 MEDICAL HOLDING APPARATUS
102 BASE
104 ARM
106 IMAGING DEVICE
110a, 110b, 110c, 110d, 110e, 110f JOINT
112a, 112b, 112c, 112d, 112e, 112f LINK
114 COUNTERWEIGHT
152 ARM UNIT
154 IMAGING UNIT
156 COMMUNICATION UNIT
158 CONTROL UNIT
160 IMAGING CONTROLLER
162 ARM CONTROLLER
164 DISPLAY CONTROLLER

The invention claimed is:

1. A medical holding apparatus comprising:
an arm including a plurality of links mutually coupled through one of joints, the arm having at least six degrees of freedom due to rotational motion about a rotation axis, the arm being configured to function as a balanced arm with a counterweight and support a medical imaging device; and
an arm control circuit configured to control motion of the arm, wherein
at least three of the joints in the arm each are provided with an angular sensor that detects a rotation angle of the rotation axis and an actuator that gives the joint an assist force of assisting the rotational motion, and
the arm control circuit is configured to
control, based on respective detected results of the angular sensors, the respective assist forces of the actuators such that an amount of force in operation to move the medical imaging device supported by the arm remains in a predetermined range of force, and
increase the amount of force in operation in conjunction with a deviation of a field of view of the medical imaging device from a predetermined range of fields of views.

2. The medical holding apparatus according to claim 1, wherein the arm control circuit is configured to control the respective assist forces of the actuators such that the amount of force in operation remains in an allowable range including a set value having been set.

3. The medical holding apparatus according to claim 1, wherein the joints each provided with the angular sensor and the actuator in the arm include three joints corresponding to a first rotation axis, a second rotation axis, and a third rotation axis from a side on which the medical imaging device is supported by the arm.

4. The medical holding apparatus according to claim 3, wherein the arm control circuit is configured to control the respective assist forces of the actuators such that the amount of force in operation is larger than an amount of force in operation in a case where no control is performed.

5. The medical holding apparatus according to claim 1, wherein the joints each provided with the angular sensor and the actuator in the arm include three joints corresponding to a first rotation axis, a second rotation axis, and a third rotation axis from a side opposite to a side on which the medical imaging device is supported by the arm.

6. The medical holding apparatus according to claim 5, wherein the arm control circuit is configured to control the respective assist forces of the actuators such that the amount of force in operation is smaller than an amount of force in operation in a case where no control is performed.

7. The medical holding apparatus according to claim 1, wherein the joints each provided with the angular sensor and the actuator in the arm include all the joints.

8. The medical holding apparatus according to claim 1, further comprising: the medical imaging device supported by the arm.

9. The medical holding apparatus according to claim 8, wherein the medical imaging device includes an imaging device that images a target to be observed.

10. The medical holding apparatus according to claim 1, wherein the arm control circuit is further configured to
determine a field of view of the imaging device;
in response to the field of view being wide, control the respective assist forces of the actuators such that the amount of force in operation remains in a first allowable range including a first set value; and
in response to the field of view being narrow, control the respective assist forces of the actuators such that the amount of force in operation remains in a second allowable range including a second set value, wherein the second set value is smaller than the first set value.

11. The medical holding apparatus according to claim 1, wherein the arm control circuit is further configured to
determine a magnification of image output by the imaging device; and
control the respective assist forces of the actuators such that the amount of force in operation remains in an allowable range including a set value, wherein the set value increases as the magnification increases.

12. The medical holding apparatus according to claim 2, wherein the set value is determined by an operation being performed.

13. A non-transitory computer readable storage device having computer readable instructions that when executed by circuitry cause the circuitry to:
control arm movement of an arm including a plurality of links mutually coupled through one of joints, the arm having at least six degrees of freedom due to rotational motion about a rotation axis, the arm being configured to function as a balanced arm with a counterweight and support a medical imaging device, including:
receiving data from at least three of the joints in the arm from an angular sensor that detects a rotation angle of the rotation axis in each of the at least three joints and an actuator that gives the joint an assist force of assisting the rotational motion;
controlling, based on respective received data from the angular sensors, respective assist forces of an actuator that gives the joint an assist force of assisting the rotational motion in each of the at least three joints, such that an amount of force in operation to move the medical imaging device supported by the arm remains in a predetermined range of force;
increasing the amount of force in operation in conjunction with a deviation of a field of view of the imaging device from a predetermined range of fields of views; and
outputting the respective assist forces to each of the actuators.

14. The non-transitory computer readable storage device according to claim 13, wherein the circuitry is further configured to
determine a field of view of the medical imaging device;
in response to the field of view being wide, control the respective assist forces of the actuators such that the amount of force in operation remains in a first allowable range including a first set value; and
in response to the field of view being narrow, control the respective assist forces of the actuators such that the amount of force in operation remains in a second allowable range including a second set value, wherein the second set value is smaller than the first set value.

15. The non-transitory computer readable storage device according to claim 13, wherein the circuitry is further configured to
determine a magnification of image output by the imaging device; and
control the respective assist forces of the actuators such that the amount of force in operation remains in an allowable range including a set value, wherein the set value increases as the magnification increases.

16. The non-transitory computer readable storage device according to claim 13, wherein the circuitry is configured to control the respective assist forces of the actuators such that the amount of force in operation remains in an allowable range including a set value having been set in accordance with an operation being performed.

17. A method for controlling arm movement of an arm including a plurality of links mutually coupled through one of joints, the arm having at least six degrees of freedom due to rotational motion about a rotation axis, the arm being configured to function as a balanced arm with a counterweight and support a medical imaging device, the method comprising:
receiving data from at least three of the joints in the arm from an angular sensor that detects a rotation angle of the rotation axis in each of the at least three joints and an actuator that gives the joint an assist force of assisting the rotational motion;
controlling, based on respective received data from the angular sensors, respective assist forces of an actuator that gives the joint an assist force of assisting the rotational motion in each of the at least three joints, such that an amount of force in operation to move the medical imaging device supported by the arm remains in a predetermined range of force;
increasing the amount of force in operation in conjunction with a deviation of a field of view of the imaging device from a predetermined range of fields of views; and outputting the respective assist forces to each of the actuators.

\* \* \* \* \*